(12) United States Patent
Inada

(10) Patent No.: US 6,306,797 B1
(45) Date of Patent: Oct. 23, 2001

(54) PLANT GROWTH REGULATOR AND PROCESS FOR PRODUCING THE SAME

(75) Inventor: Sinichi Inada, Chiba pref. (JP)

(73) Assignee: Jollive Co., Ltd., Chiba (JP)

( * ) Notice: Subject to any disclaimer, the term of this patent is extended or adjusted under 35 U.S.C. 154(b) by 0 days.

(21) Appl. No.: 09/534,114

(22) Filed: Mar. 23, 2000

(51) Int. Cl.$^7$ .................. A01N 25/30; A01N 35/06; A01N 65/00

(52) U.S. Cl. ............... 504/116.1; 504/348; 504/362; 514/690; 514/975; 424/195.1

(58) Field of Search ................. 504/116.1, 348, 504/362; 514/690, 975; 424/195.1

(56) References Cited

U.S. PATENT DOCUMENTS

| | | | |
|---|---|---|---|
| 4,599,233 | * | 7/1986 | Misato et al. .......... 424/127 |
| 5,723,110 | * | 3/1998 | Yamamoto et al. ........ 424/65 |
| 5,747,049 | * | 5/1998 | Tominaga et al. ....... 424/401 |
| 5,756,542 | * | 5/1998 | Kojima et al. .......... 514/514 |

* cited by examiner

Primary Examiner—S. Mark Clardy
(74) Attorney, Agent, or Firm—Nixon & Vanderhye P.C.

(57) ABSTRACT

A solubilized plant growth regulator includes a mixture mainly containing a hiba oil, ethanol, polyoxyethylene sorbitan monolaurate or another surfactant or a nonionic surfactant prepared from a higher alcohol. Alternatively, such a solubilized plant growth regulator includes a stirred mixture mainly containing a hiba oil, a sucrose fatty acid ester, ethanol, propylene glycol, polyoxyethylene sorbitan monolaurate or a nonionic surfactant prepared from a higher alcohol, and water. The plant growth regulator has substantially no toxicity to the human body and high insecticidal/insect-repellant and antimicrobial activities.

8 Claims, No Drawings

PLANT GROWTH REGULATOR AND PROCESS FOR PRODUCING THE SAME

BACKGROUND OF THE INVENTION

1. Field of the Invention

The present invention relates to a solubilized plant growth regulator having a insecticidal/insect-repellent activity and antimicrobial activity and mainly comprising a hiba oil and a surfactant. Further, the present invention relates to a solubilized plant growth regulator having a insecticidal/insect-repellent activity and antimicrobial activity and containing, for example, a sucrose fatty acid ester, ethanol, and propylene glycol, in addition to the aforementioned main components.

Such surfactants include, but are not limited to, polyoxyethylene sorbitan monolaurate and nonionic surfactants prepared from higher alcohols.

2. Description of the Related Art

A variety of plant growth regulators have been developed. Such plant growth regulators should have toxicity against noxious or injurious animals but should have no influence on the other organisms than the injurious animals.

Of numerous plant growth regulators prepared from inorganic or organic compounds, plant growth regulators using a hiba oil or hinokitiol for obtaining higher insecticidal/insect-repellent and antimicrobial activities are few in number.

Especially, no solubilized plant growth regulator comprising a hiba oil and having insecticidal/insect-repellent and antimicrobial activities has been developed.

Such plant growth regulators have toxicity against noxious or injurious animals and must be as harmless and nontoxic to the other organisms than injurious animals as possible.

In addition, demands have been made to provide plant growth regulators having insecticidal/insect-repellent and antimicrobial activities, which are composed of harmless natural products and no other.

Specifically, plant growth regulators having a high safety and a very high effect have been demanded.

SUMMARY OF THE INVENTION

Accordingly, an object of the invention is to solve the above problems and to provide a plant growth regulator mainly including components that are harmless in the human body and having insecticidal/insect-repellent and antimicrobial activities by action of hinokitiol or a hiba oil, which plant growth regulator is solubilized and can be more efficiently applied to a plant.

Specifically, the invention provides, according to a first aspect, a plant growth regulator including a mixture of 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of polyoxyethylene sorbitan monolaurate, and 0% by weight to 74.9% by weight of water. The plant growth regulator is solubilized and has a total content of the sucrose fatty acid ester and the polyoxyethylene sorbitan monolaurate in a range from 15% by weight to 89.9% by weight.

According to a second aspect, the invention provides a plant growth regulator which includes a mixture of 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of a nonionic surfactant prepared from a higher alcohol, and 0% by weight to 74.9% by weight of water. The plant growth regulator is solubilized and has a total content of the sucrose fatty acid ester and the nonionic surfactant prepared from a higher alcohol in a range from 15% by weight to 89.9% by weight.

The invention provides, according to a third aspect, a plant growth regulator which is solubilized and includes a mixture of 0.1% by weight to 50% by weight of a hiba oil, 5% by weight to 15% by weight of ethanol, 5% by weight to 15% by weight of propylene glycol, 15% by weight to 89.9% by weight of polyoxyethylene sorbitan monolaurate, and 0% by weight to 74.9% by weight of water.

In a fourth aspect, the invention provides a plant growth regulator which is solubilized and includes a mixture of 0.1% by weight to 50% by weight of a hiba oil, 5% by weight to 15% by weight of ethanol, 5% by weight to 15% by weight of propylene glycol, 15% by weight to 89.9% by weight of a nonionic surfactant prepared from a higher alcohol, and 0% by weight to 74.9% by weight of water.

The invented plant growth regulator may be, according to a fifth aspect, a Plant growth regulator which is solubilized and includes a mixture of 0.1% by weight to 45% by weight of a hiba oil, 5% by weight to 15% by weight of ethanol, 10% by weight to 20% by weight of sorbitan monolaurate, 40% by weight to 60% by weight of polyoxyethylene sorbitan monolaurate, and 0% by weight to 44.9% by weight of water.

Further, the invention provides, according to a sixth aspect, a plant growth regulator which is solubilized and includes a mixture of 0.1% by weight to 45% by weight of a hiba oil, 5% by weight to 15% by weight of ethanol, 10% by weight to 20% by weight of a nonionic surfactant prepared from a higher alcohol, 40% by weight to 60% by weight of another nonionic surfactant prepared from a higher alcohol, and 0% by weight to 44.9% by weight of water. In other words, the plant growth regulator may include two species of surfactants.

Such a solubilized plant growth regulator may be produced by a process for producing a plant growth regulator according to a seventh aspect. The process includes the steps of mixing 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of polyoxyethylene sorbitan monolaurate, and 0% by weight to 74.9% by weight of water to yield a mixture, in which the total content of the sucrose fatty acid ester and the polyoxyethylene sorbitan monolaurate is in a range from 15% by weight to 89.9% by weight, and stirring the mixture at a temperature of about 30° C. or higher to yield a solubilized plant growth regulator.

In addition and advantageously, such a solubilized plant growth regulator may also be obtained by a process for producing a plant growth regulator according to an eighth aspect. The process includes the steps of mixing and stirring 10% by weight to 20% by weight of a nonionic surfactant prepared from a higher alcohol and 0% by weight to 44.9% by weight of water to yield an emulsion or a solubilized solution and adding 0.1% by weight to 45% by weight of a hiba oil, 5% by weight to 15% by weight of ethanol, and 40% by weight to 60% by weight of another nonionic surfactant prepared from a higher alcohol to the emulsion or solution to yield a solubilized plant growth regulator.

DESCRIPTION OF THE PREFERRED EMBODIMENT

The invented plant growth regulator can be obtained by mixing and stirring main components, a hiba oil, ethanol, and polyoxyethylene sorbitan monolaurate or another surfactant or a nonionic surfactant prepared from a higher alcohol, and solubilizing the resulting mixture.

The present inventors focused attention on an insecticidal activity and an antimicrobial activity of a hiba oil and devised to use the hiba oil in a plant growth regulator. However, they found that a plant growth regulator including the hiba oil alone cannot be homogeneously and efficiently applied onto a plant.

Accordingly, the invention is also intended to provide a solubilized plant growth regulator as a solution containing a mixture of the hiba oil and a surfactant.

The present inventors found that such a solubilized plant growth regulator can be obtained by incorporating 50% by weight or more of a surfactant in the solution.

The invented plant growth regulator is not limited to the solubilized plant growth regulator and also includes an emulsified plant growth regulator in which materials are mixed to some extent. Such an emulsified plant growth regulator can be diluted for spraying and can efficiently and homogeneously spray the hiba oil to a plant.

These solutions and emulsions have been provided focusing attention on the insecticidal and antimicrobial activities of the hiba oil, but the advantages of the invented plant growth regulators are not limited to such activities. The results obtained in experiments showed that spraying of the invented plant growth regulator on a plant not only can repel insect pest but also can enhance the growth of the plant. The use of the invented plant growth regulator also makes the plant leafy and increases the number of petals of a petaliferous plant, and in addition, makes a crop plant yield very well.

The surfactants for use in the invention include, but are not limited to, polyoxyethylene sorbitan monolaurate, as well as ethylene oxide-based surfactants, polyhydric alcohol-based surfactants, and other nonionic surfactants.

Such nonionic surfactants include, for example, polyoxyethylene oleic esters; nonylphenyl ethers, octyiphenyl ethers, dodecylphenyl ethers, and other alkylphenyl ethers; and natural or synthetic nonionic surfactants prepared from higher alcohols.

The surfactants should preferably have a hydrophile-lipophile balance (HLB) of 10 or more.

The emulsified or solubilized plant growth regulator in an embodiment can be obtained by mixing and stirring 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of polyoxyethylene sorbitan monolaurate, and 0% by weight to 74.9% by weight of water. The stirring operation should preferably be performed at temperatures of about 30° C. or higher to facilitate the emulsification or solubilization.

Likewise, the invented emulsified or solubilized plant growth regulator can also be obtained by the use of a nonionic surfactant prepared from a higher alcohol instead of the polyoxyethylene sorbitan monolaurate.

These invented plant growth regulators have substantially no toxicity to the human body and invite no trouble even when the regulators come in contact with the human body. When the invented plant growth regulator is diluted, for example, about 3000 times and is spread to a plant, the spread plant growth regulator can repel insect pest and therefore has a very efficient insecticidal/insect-repellent activity. This is probably because of the effect of hinokitiol or the hiba oil.

In addition, the antimicrobial activity of the plant growth regulator can regulate, and can highly enhance, the growth of the plant.

The invented plant growth regulator is emulsified or solubilized by action of the above composition and the process, and can be homogeneously and thoroughly applied to overall the target plant.

The invented plant growth regulator preferably has a composition of 0.1% by weight to 50% by weight of a hiba oil, 1% by weight to 30% by weight of a sucrose fatty acid ester, 5% by weight to 45% by weight of ethanol, 5% by weight to 45% by weight of propylene glycol, 15% by weight to 88.9% by weight of polyoxyethylene sorbitan monolaurate, and 0% by weight to 74.9% by weight of water.

In this preferred composition, a solubilized plant growth regulator can be obtained by incorporating about 20% by weight or more of the polyoxyethylene sorbitan monolaurate component.

Alternatively, an emulsified plant growth regulator can be obtained by incorporating about 10% by weight or more of the polyoxyethylene sorbitan monolaurate component.

The use of a nonionic surfactant prepared from a higher alcohol instead of the polyoxyethylene sorbitan monolaurate component in this embodiment can also yield the invented Plant growth regulator. A content of the nonionic surfactant of about 10% by weight or more can yield an emulsified plant growth regulator, and a content of the nonionic surfactant of about 15% by weight or more can yield a substantially solubilized plant growth regulator.

The emulsified or solubilized plant growth regulator can also be obtained by mixing 0.1% by weight to 50% by weight of a hiba oil, 5% by weight to 45% by weight of ethanol, 5% by weight to 45% by weight of propylene glycol, 10% by weight to 89.9% by weight of polyoxyethylene sorbitan monolaurate, and 0% by weight to 79.9% by weight of water.

The invented emulsified or solubilized plant growth regulator can also have a composition of 0.1% by weight to 45% by weight of a hiba oil or hinokitiol, 5% by weight to 15% by weight of ethanol, 10% by weight to 20% by weight of sorbitan monolaurate, 40% by weight to 60% by weight of polyoxyethylene sorbitan monolaurate, and 0% by weight to 44.9% by weight of water.

According to this composition, the sorbitan monolaurate and/or the polyoxyethylene sorbitan monolaurate component can be replaced with a nonionic surfactant prepared from a higher alcohol.

The term "hiba oil" as used herein means and includes essential oils obtained by the steam distillation of lumbers and scrap lumbers of, for example, Thujopsis dolabrata, Chamaecyparis taiwanensis, Western red cedar, and other wood containing hinokitiol, as well as distillated water from these plants, and natural or synthesized hinokitiol.

The content of the hiba oil in the invented plant growth regulator should range from 0.1% by weight to 50% by weight. Within this range, the plant growth regulator is solubilized by adjusting the contents of the other components, or else, is emulsified particularly by adjusting the content of the surfactant component.

The content of the surfactant component is selected within a range from 1% by weight to 88.9% by weight, and largely affects whether the resulting plant growth regulator is emulsified or solubilized.

For example, the use of the surfactant component in a content of about 1% by weight to about 15% by weight may yield an emulsified plant growth regulator in many cases.

In this connection, a hydrophilic surfactant having a high HLB enhances the solubilization.

A content of the surfactant component of from about 16% by weight to about 30% by weight yields a somewhat solubilized plant growth regulator, while the degree of solubilization also depends on the composition of the other components.

A content of the surfactant component of from about 31% by weight to about 88.9% by weight can yield a substantially solubilized plant growth regulator.

Particularly, when the nonionic surfactant prepared from a higher alcohol or polyethylene sorbitan monolaurate is used, the resulting plant growth regulator has a very high infiltration capacity. This type of plant growth regulator can be readily absorbed by leaves, stems, and other parts of a plant when the regulator is applied to the plant, and can sufficiently and rapidly exhibit its activities.

The hiba oil is used in a content ranging from 0.1% by weight to 50% by weight in the invented plant growth regulator, and the resulting plant growth regulator can be solubilized even when the hiba oil occupies 50% by weight in the plant regulator, by appropriately adjusting the content of the surfactant component, as described above.

Accordingly, a solubilized plant growth regulator can be obtained by appropriately adjusting the content of the surfactant component according to the content of the hiba oil.

The advantages of the use of the hiba oil will exhibit according to the content of the hiba oil. For example, when the content of the hiba oil is in a range from about 0.1% by weight to 3% by weight, the effects of the hiba oil are obtained to some extent and its antimicrobial and insecticidal/insect-repellent activities are higher than those of conventional equivalents. In this case, the effects are somewhat lower than those of the invented plant growth regulators having a higher content of the hiba oil.

A content of the hiba oil in a range from about 4% by weight to about 15% by weight can effectively exhibit high insecticidal/insect-repellent and antimicrobial activities of the hiba oil. This range of the content of the hiba oil can most effectively exhibit the effects of the hiba oil. In other words, advantages of the use of the hiba oil can be effectively obtained with a relatively low content of the hiba oil within this range.

Alternatively, a content of the hiba oil in a range from about 16% by weight to about 30% by weight can also effectively yield satisfactory advantages.

A content of the hiba oil in a range from about 31% by weight to about 50% by weight yields very satisfactory advantages of the hiba oil but the resulting plant growth regulator is liable to be emulsified to some extent.

In this connection, the results in experiments show that the use of polyoxyethylene sorbitan monolaurate enhances the solubilization of the resulting plant growth regulator even if the content of the hiba oil is increased.

The invented plant growth regulator configured and solubilized or emulsified as above is used in practice by diluting, for example, from about 1000 times to about 3000 times and is applied to a plant in raising of seeding and in fix planting.

The plant growth regulator can be also employed in foliar application and in soil amelioration.

The invention will be further illustrated in detail with reference to several inventive examples below, which are not intended to limit the scope of the invention.

EXAMPLE 1

A solubilized plant growth regulator was prepared by mixing and stirring 10% by weight of a hiba oil, 10% by weight of a sucrose fatty acid ester, 25% by weight of ethanol, 25% by weight of propylene glycol, and 30% by weight of polyoxyethylene sorbitan monolaurate.

The sucrose fatty acid ester used in this example was RYOTO SUGAR ESTER LWA-1570 (trade name, a product of MITSUBISHI-KAGAKU FOODS CORPORATION, Japan), and the polyoxyethylene sorbitan monolaurate was IONET T20-C (trade name, a product of Sanyo Chemical Industries, Ltd., Japan).

EXAMPLE 2

A solubilized plant growth regulator was prepared by mixing and stirring 10% by weight of a hiba oil, 10% by weight of ethanol, 60% by weight of polyoxyethylene sorbitan monolaurate, and 20% by weight of water.

The polyoxyethylene sorbitan monolaurate used herein was IONET T20-C (trade name, a product of Sanyo Chemical Industries, Ltd., Japan).

EXAMPLE 3

A solubilized plant growth regulator was prepared in the following manner. Initially, 50% by weight of polyoxyethylene sorbitan monolaurate and 20% by weight of water were mixed and stirred to yield a solution A. Separately, 10% by weight of a hiba oil, 10% by weight of ethanol, and 10% by weight of sorbitan monolaurate were mixed and stirred to yield a solution B. The solution A was then added to and stirred with the solution B to yield a solubilized plant growth regulator.

The polyoxyethylene sorbitan monolaurate used herein was IONET T20-C (trade name, a product of Sanyo Chemical Industries, Ltd., Japan), and the sorbitan monolaurate was IONET S20 (trade name, a product of Sanyo Chemical Industries, Ltd., Japan).

EXAMPLE 4

A solubilized plant growth regulator was prepared by mixing 10% by weight of a hiba oil, 10% by weight of ethanol, 20% by weight of propylene glycol, 10% by weight of a nonionic surfactant prepared from a higher alcohol and having a hydrophilelipophile balance (HLB) of 12.2, 5% by weight of another nonionic surfactant prepared from a higher alcohol and having an HLB of 13.4, and 45% by weight of water, and stirring the resulting mixture at a temperature of 30° C.

The nonionic surfactant prepared from a higher alcohol and having a hydrophile-lipophile balance (HLB) of 12.2 was DKS NL-70 (trade name, a product of Daiichi Kogyo Seiyaku Co., Ltd., Japan) and the nonionic surfactant prepared from a higher alcohol and having an HLB of 13.4 was DKS NL-90 (trade name, a product of Daiichi Kogyo Seiyaku Co., Ltd., Japan).

EXAMPLE 5

A solubilized plant growth regulator was prepared by mixing 10% by weight of a hiba oil, 32% by weight of a sucrose fatty acid ester, 25% by weight of ethanol, 25% by weight of propylene glycol, and 8% by weight of polyoxyethylene sorbitan monolaurate and stirring the resulting mixture at a temperature of about 30° C.

The sucrose fatty acid ester used in this example was RYOTO SUGAR ESTER LWA-1570 (trade name, a product of MITSUBISHI-KAGAKU FOODS CORPORATION, Japan), and the polyoxyethylene sorbitan monolaurate was IONET T20-C (trade name, a product of Sanyo Chemical Industries, Ltd., Japan).

EXAMPLE 6

A solubilized plant growth regulator was prepared by mixing 10% by weight of a hiba oil, 15% by weight of a sucrose fatty acid ester, 25% by weight of ethanol, 25% by weight of propylene glycol, and 25% by weight of polyoxyethylene sorbitan monolaurate.

The sucrose fatty acid ester used in this example was RYOTO SUGAR ESTER LWA-1570 (trade name, a product of MITSUBISHI-KAGAKU FOODS CORPORATION, Japan), and the polyoxyethylene sorbitan monolaurate was IONET T20-C (trade name, a product of Sanyo Chemical Industries, Ltd., Japan).

Other embodiments and variations will be obvious to those skilled in the art, and this invention is not to be limited to the specific matters stated above.

What is claimed is:

1. A plant growth regulator comprising a mixture of 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of polyoxyethylene sorbitan monolaurate, and 0% by weight to 74.9% by weight of water, wherein the total content of the sucrose fatty acid ester and the polyoxyethylene sorbitan monolaurate is in a range from 15% by weight to 89.9% by weight, and said plant growth regulator is solubilized.

2. A plant growth regulator comprising a mixture of 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of a nonionic surfactant prepared from a higher alcohol, and 0% by weight to 74.9% by weight of water, wherein the total content of the sucrose fatty acid ester and the nonionic surfactant prepared from a higher alcohol is in a range from 15% by weight to 89.9% by weight, and said plant growth regulator is solubilized.

3. A plant growth regulator comprising a solubilized mixture of 0.1% by weight to 50% by weight of a hiba oil, 5% by weight to 15% by weight of ethanol, 5% by weight to 15% by weight of propylene glycol, 15% by weight to 89.9% by weight of polyoxyethylene sorbitan monolaurate, and 0% by weight to 74.9% by weight of water.

4. A plant growth regulator comprising a solubilized mixture of 0.1% by weight to 50% by weight of a hiba oil, 5% by weight to 15% by weight of ethanol, 5% by weight to 15% by weight of propylene glycol, 15% by weight to 89.9% by weight of a nonionic surfactant prepared from a higher alcohol, and 0% by weight to 74.9% by weight of water.

5. A plant growth regulator comprising a solubilized mixture of 0.1% by weight to 45% by weight of a hiba oil, 5% by weight to 15% by weight of ethanol, 10% by weight to 20% by weight of sorbitan monolaurate, 40% by weight to 60% by weight of polyoxyethylene sorbitan monolaurate, and 0% by weight to 44.9% by weight of water.

6. A plant growth regulator comprising a solubilized mixture of 0.1% by weight to 45% by weight of a hiba oil, 5% by weight to 15% by weight of ethanol, 10% by weight to 20% by weight of a nonionic surfactant prepared from a higher alcohol, 40% by weight to 60% by weight of another nonionic surfactant prepared from a higher alcohol, and 0% by weight to 44.9% by weight of water.

7. A process for producing a plant growth regulator, said process comprising the steps of:

mixing 0.1% by weight to 50% by weight of a hiba oil, 1% by weight to 39% by weight of a sucrose fatty acid ester, 5% by weight to 45% by weight of ethanol, 5% by weight to 45% by weight of propylene glycol, 1% by weight to 88.9% by weight of polyoxyethylene sorbitan monolaurate, and 0% by weight to 74.9% by weight of water to yield a mixture, the total content of the sucrose fatty acid ester and the polyoxyethylene sorbitan monolaurate being in a range from 15% by weight to 89.9% by weight; and stirring said mixture at a temperature of about 30° C. or higher to solubilize said mixture.

8. A process for producing a plant growth regulator comprising the steps of:

mixing and stirring 10% by weight to 20% by weight of a nonionic surfactant prepared from a higher alcohol and 0% by weight to 44.9% by weight of water to yield an emulsion or a solubilized solution;

and adding 0.1% by weight to 45% by weight of a hiba oil, 5% by weight to 15% by weight of ethanol, and 40% by weight to 60% by weight of another nonionic surfactant prepared from a higher alcohol to said emulsion or said solution to yield a solubilized plant growth regulator.

* * * * *